United States Patent [19]
Foote

[11] Patent Number: 4,729,960
[45] Date of Patent: Mar. 8, 1988

[54] METHOD OF PROSPECTING FOR HYDROCARBON DEPOSITS

[76] Inventor: Robert S. Foote, 1328 Etain, Irving, Tex. 75060

[21] Appl. No.: 807,495

[22] Filed: Dec. 11, 1985

Related U.S. Application Data

[63] Continuation-in-part of Ser. No. 743,391, Jun. 11, 1985, abandoned.

[51] Int. Cl.$^4$ ............................................. G01N 33/24
[52] U.S. Cl. ......................................... 436/31; 166/248
[58] Field of Search ........................... 436/31; 166/248

[56] References Cited

U.S. PATENT DOCUMENTS

| | | | |
|---|---|---|---|
| 2,104,743 | 1/1938 | Herrick | 324/377 |
| 2,225,248 | 12/1940 | Lewis et al. | 324/376 |
| 2,296,852 | 9/1942 | Horner | 436/31 |
| 2,310,291 | 2/1943 | Horvitz | 436/31 |
| 2,634,317 | 4/1953 | Marchand et al. | 324/377 |
| 2,665,332 | 1/1954 | Weiss et al. | 324/377 |
| 2,725,281 | 11/1955 | Bond | 436/31 |
| 3,890,563 | 6/1975 | Dowling et al. | 324/340 |
| 4,344,842 | 8/1982 | Fox | 585/850 |
| 4,360,359 | 11/1982 | Oehler | 436/31 |

FOREIGN PATENT DOCUMENTS 0952951 8/1974 Canada ............................. 324/201

*Primary Examiner*—Kenneth M. Schor
*Assistant Examiner*—Lori-Ann Cody
*Attorney, Agent, or Firm*—Kanz, Scherback & Timmons

[57] ABSTRACT

Disclosed are methods of prospecting for subterranean deposits of hydrocarbon. Earth samples are taken at various depths in a substantially vertical column of earth overlying an area suspected of containing an underground petroliferous deposit. The magnetic susceptibility of each sample is then measured (or the concentration of maghemite or greigite therein determined) to determine the relative concentration of diagenetic magnetic material therein. The relative concentration data is correlated with depth from the surface to the approximate maximum penetration depth of surface-related oxygen. An anomaly occurring in the curve produced by such correlation demonstrates the likelihood of discovering a subterranean deposit therebelow. The relative concentration of diagenetic magnetic material in the earth's surface within the layer thereof subject to surface water penetration is increased by oxidation of ferrous iron previously reduced from the ferric to the ferrous state by the reducing effect of upwardly migrating hydrocarbons diffusing toward the surface from a subterranean deposit thereof.

37 Claims, 4 Drawing Figures

METHOD OF PROSPECTING FOR HYDROCARBON DEPOSITS

This is a continuation-in-part of application Ser. No. 743,391 filed June 11, 1985 and now abandoned.

This invention relates to methods of prospecting for subterranean deposits of hydrocarbons. More particularly, it relates to methods of using variations in concentrations of near-surface magnetic materials to determine the likelihood of finding subterranean hydrocarbon deposits therebelow.

The following disclosure is offered for public dissemination in return for grant of a patent. Although it is sufficiently detailed to provide full understanding of the principles of the invention, this disclosure is not intended to prejudice the purpose of a patent which is to protect each new inventive concept therein no matter how others may later disguise it by variations in form, additions or further improvements.

It is well-known that iron (Fe) is distributed in varying quantities throughout the earth's crust. As noted by Horvitz, U.S. Pat. No. 2,310,191, Fe in the earth's crust ordinarily appears in compounds in the ferric (Fe+++) valence state. However, ferric iron distributed over a subterranean deposit of hydrocarbons is gradually reduced to form new compounds in which the iron is in the ferrous (Fe++) valence state by the reducing effect of hydrocarbons migrating from the hydrocarbon deposit to the surface. Horvitz thus concluded that the likelihood of discovering subterranean deposits of hydrocarbon could be enhanced by logging the relative concentration of ferrous compounds in earth samples taken from a borehole and discovered that iron in the reduced state increased in concentration from the earth's surface to the producing horizon. Such logging is, of course, useful as an aid in forecasting likelihood of success in finding a hydrocarbon deposit as a borehole progresses, but is not particularly useful as a surface or near-surface prospecting tool.

It is also well-known that free iron and certain iron compounds exhibit magnetic characteristics. It has now been discovered that correlation of the concentration of magnetic compounds to depth from the earth's surface can be used as the basis for prospecting for subterranean deposits of hydrocarbons.

The underlying principle upon which the present invention is based is the discovery that diagenetically-created magnetic materials are formed in the earth's surface and near-surface by the oxidation of ferrous or free iron previously reduced from the ferric state by the reducing environment of hydrocarbons migrating and/or diffusing from an underground deposit thereof. Since these materials exhibit magnetic characteristics, their presence can be determined with airborne or surface magnetometers. Unfortunately, magnetic anomalies detected near the surface do not necessarily indicate the presence of subterranean deposits of hydrocarbons. Obviously, since iron is distributed in various amounts throughout the earth's crust, various forms of magnetic iron compounds can be formed or placed at the earth's surface and near-surface by various environmental and geological conditions totally unrelated to the presence or absence of subterranean hydrocarbon deposits. Furthermore, mere detection of magnetic anomalies at or near the earth's surface cannot determine the chemical composition of the magnetic material or distinguish the relative distribution of such anomalies with depth from the surface.

It has now been discovered that the relative concentration of diagenetic magnetic material containing iron (previously reduced by the reducing environment above a subterranean hydrocarbon deposit) is detectable and demonstrates a distinctly recognizable distribution. This distribution is directly related to the oxidizing conditions present in the near-surface, particularly that portion of the earth's surface subject to penetration by surface water or other surface originated oxidizing conditions and thus enriched in oxygen. Within each geologically-formed earth strata, the relative concentration of magnetic material (vertically) does not ordinarily vary dramatically with distance from the surface. However, the relative concentration thereof does demonstrate a distinct distribution with distance from the surface over a subterranean deposit of hydrocarbon.

Since the upward migration of hydrocarbons continuously reduces ferric iron compounds in the overburden above a hydrocarbon deposit, and since the iron reduced by the upward migration of such reducing hydrocarbons in the near-surface zone is subject to penetration by surface water, it is continuously oxidized to produce higher concentrations of diagenetic magnetic materials. Thus an observable discontinuity in relative magnetic intensity occurs approximately near the maximum penetration depth of surface water containing dissolved oxygen from the atmosphere in the earth's surface directly above a deposit of hydrocarbons.

In accordance with the invention, the relative concentration of magnetic material is determined in earth samples taken at various depths from the surface in a borehole drilled in an area suspected to contain a hydrocarbon deposit. The relative magnetic susceptibility data are then correlated to depth from the surface and the approximate maximum depth of surface water penetration is determined. A higher-than-normal concentration in the distribution of background magnetic material (as determined by magnetic susceptibility of the borehole samples) down to the approximate maximum depth of oxygen-rich surface water penetration indicates a strong likelikhood that a deposit of hydrocarbons presently exists or has previously existed at a deeper horizon in the locale of the borehole. The invention thus provides means for charting the surface outline of known deposits without drilling holes substantially deeper than the oxygen-rich surface water penetration depth. The invention also provides means for substantially enhancing the likelihood of finding hydrocarbon deposits in areas suspected of containing the same. The method of the invention may be used in all types of surface terrain including underwater terrain and is substantially less expensive than drilling a test hole to the depth of the suspected deposit. Other features and advantages of the invention will become more readily apparent from the following detailed description taken in connection with the appended claims and attached drawings in which:

Because of the decreasing known petroleum supply and everincreasing demand for petroleum products, many wide and varying techniques have been developed for prospecting for underground petroliferous deposits. Each method has its own peculiar advantages and disadvantages. However, once an area of has been determined by any of various techniques to be the potential site of an underground deposit, there can be no absolute assurance of discovering a producible well until a test hole has actually been drilled. A test hole to the suspected depth of the deposit can be, of course, quite expensive. It is therefore desirable that alternate means be developed for enhancing the likelihood of discovering such deposit before the expense of a deep test hole is incurred. The present invention is not represented to be an absolute assurance of determining the location of an underground deposit. However, once a site suspected of containing such a deposit has been identified by other means, the method of the invention may be employed in order to substantiate and determine those sites in which the discovery of an underground deposit of hydrocarbons is substantially more likely.

In practicing the invention, earth samples are taken at various depths in the near-surface immediately above the suspected deposit. The samples may be obtained by any of various of conventional means, such as drilling a shallow test hole and taking samples of drill cuttings obtained from various known depths. The magnetic susceptibility of each sample is then determined using conventional analytical equipment.

The approximate maximum depth of creation of anomalous diagenetic magnetic material at the site can be determined by various means, such as by an analysis of the drill cuttings, reference to other known geological data regarding the site and the like. Since the invention relies on determining the distribution of diagenetic magnetic materials presumed to be produced by oxidation of ferrous iron by surface or near-surface conditions, the surface water penetration depth may ordinarily be taken as a convenient measure of the depth to which oxidation should be expected to occur. The depth of surface water penetration, of course, may vary widely from site to site depending on the geologic structure of the near-surface crust. In some areas the surface water penetration may be very shallow while in other geologic formations the surface water penetration may extend hundreds of feet. However, since the principles of the invention are based on the determination of relative concentrations of diagenetically formed magnetic materials presumed to be formed by the near-surface oxidation of ferrous iron previously reduced by the upward migration of hydrocarbons, the test hole should be drilled to at least near the maximum depth of surface water penetration and preferrably to a depth greater than the maximum depth of surface water penetration.

Figure 1:
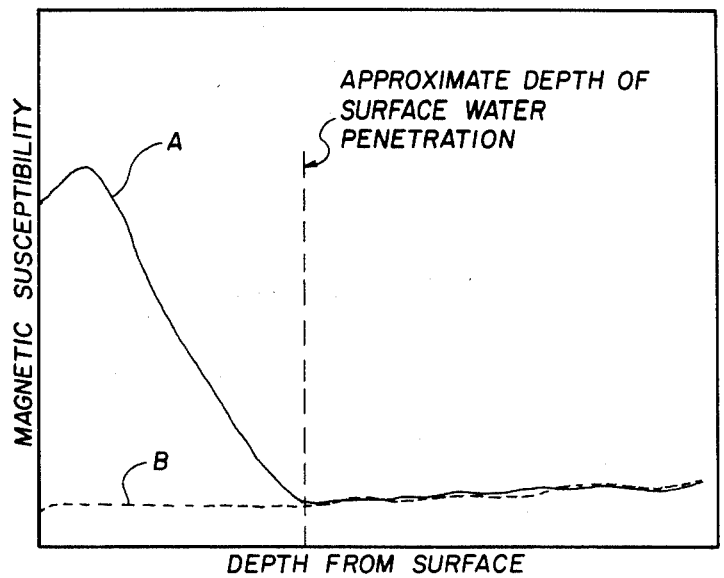
FIG. 1 is a representative graph depicting normalized curves of magnetic susceptibility of earth samples as a function of depth from the earth's surface in a column of overburden directly above a subterranean deposit of hydrocarbons.

Diagenetic magnetic materials ordinarily only appear in the near-surface of the earth's crust. The relative intensity of magnetic susceptibility of borehole samples will ordinarily remain relatively constant or increase gradually with depth at depths below the level of maximum penetration of surface water as controlled by the sedimentary materials. The magnetic susceptibility of each earth sample is then correlated with depth from the surface such as by plotting magnetic susceptibility as a function of depth. In areas overlying a subterranean deposit of hydrocarbons, the relative concentration of diagenetic magnetic material will ordinarily be substantially higher in the near-surface portion subject to surface-related oxidation than at deeper levels. Thus by plotting magnetic susceptibility of the samples versus depth, a normalized curve can be prepared which will demonstrate an anomalous magnetic susceptibility increase down to the approximate depth at which the ferrous iron (reduced by upward migration and/or diffusion of hydrocarbons) has been oxidized by surface-originating conditions. FIG. 1 represents a normalized curve demonstrative of such data.

In FIG. 1 curve A depicts a normalized curve obtained by plotting magnetic susceptibility of earth samples as a function of depth from the earth's surface in the near-surface column of earth directly over a known producing field. Note that curve A shows a generally decreasing relative concentration of magnetic susceptibility with distance from the earth's surface to the approximate maximum depth of surface water penetration. After reaching the approximate maximum depth, the curve forms a substantially straight line indicating substantially constant (or gradually increasing) concentration with respect to depth. Thus a discontinuity in the relative concentration distribution curve appears in the vicinity of the approximate maximum depth presumed to be controlled by surface water penetration. Curve B (represented by a dashed line in FIG. 1) illustrates a normalized curve of magnetic susceptibility of earth samples with respect to depth taken from a borehole in the same vicinity as the borehole from which the samples for curve A were taken. Although the borehole from which the samples were taken to generate the data curve B was drilled to the same depth as the producing well of curve A, this well proved to be a dry hole. Comparing curves A and B dramatically illustrates that although the holes were drilled in practically identical geological formations, there is a noticeable increase in a relative concentration of magnetic material in the near-surface above the subterranean deposit of hydrocarbon. Since there were no hydrocarbons migrating through the near-surface from which the samples were taken to generate the data for curve B, there is little or no observable increase in diagenetic magnetic materials above the maximum depth of surface water penetration.

Figure 2:
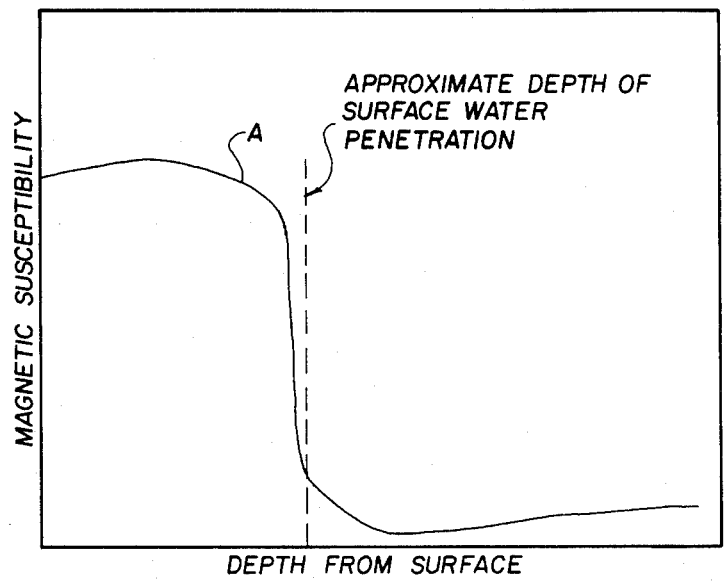
FIG. 2 is a representative graph depicting another normalized curve of magnetic susceptibility of earth sample as a function of depth over another deposit.

It has been found that the distribution of diagenetic magnetic materials above a subterranean hydrocarbon deposit may vary widely depending upon the composition and depth of the layer subject to surface-related oxidation. For example, curve A in FIG. 2 demonstrates another normalized curve produced by the same method described hereinabove with respect to FIG. 1. Curve A of FIG. 2 represents the relative magnetic susceptibility of samples with respect to depth taken in a borehole formed directly above another proven hydrocarbon deposit. Note that in curve A of FIG. 2, the relative concentration of magnetic materials remains relatively high and relatively constant throughout a major portion of the surface layer subject to surface water penetration but drops sharply as the boundary of the surface water penetration depth is crossed. Thus two distinct dicontinuities are observed in the curve. Since both appear near the depth of maximum surface water penetration, the presence of an underground deposit of hydrocarbons is again indicated.

Figure 3:
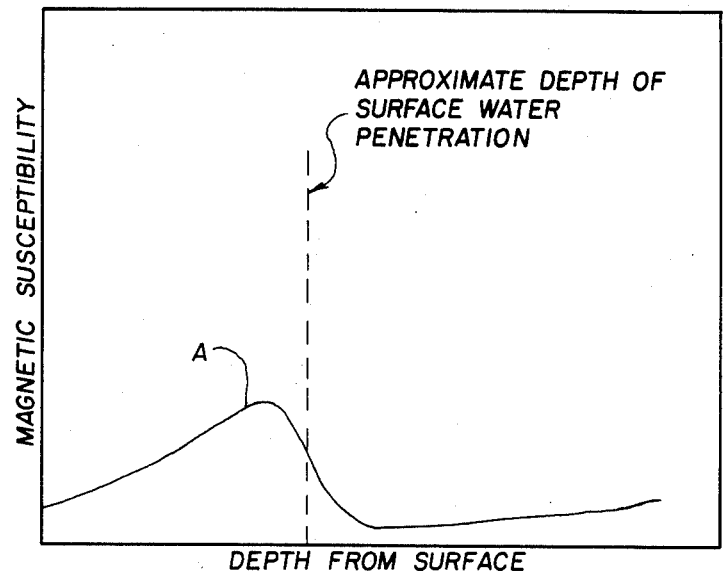
FIG. 3 is a representative graph depicting another normalized curve of magnetic susceptibility of earth sample as a function of depth over another such deposit.

In FIG. 3 the relative concentration of magnetic materials increases with depth from the surface until the region of maximum surface water penetration is reached. The relative distribution curve then drops to a relatively constant level.

Figure 4:
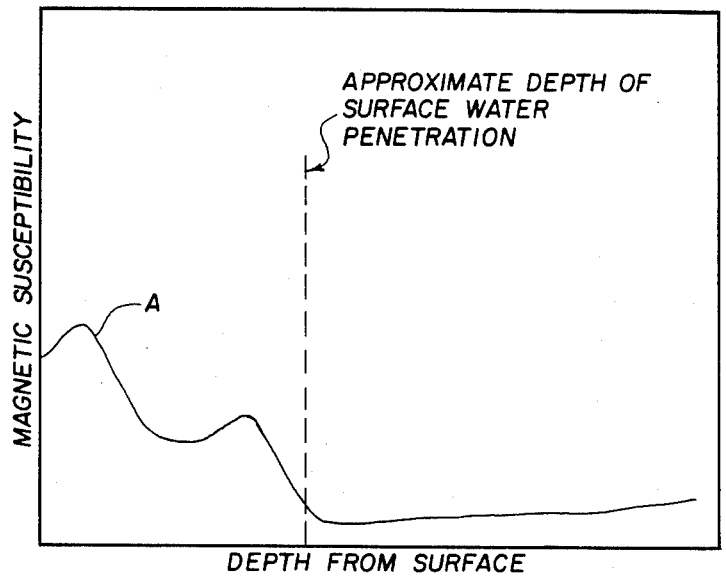
FIG. 4 is a representative graph depicting another normalized curve of magnetic susceptibility of earth sample as a function of depth over another such deposit.

FIG. 4 illustrates a normalized curve of magnetic susceptibility obtained characteristic of a near-surface region subject to surface water oxidation but which contains a plurality of geologic strata. While the curve shows two rather distinct peaks, both appear within the near-surface region subject to surface water penetration. Since the various geologic strata contain differing concentrations of geologic ferric iron compounds, the actual concentration of diagenetic magnetic materials also varies. However, the general slope of the curve representing diagenetic magnetic materials in the region subject to atmospheric oxidation still clearly indicates that the reduction and oxidation process is occurring. Thus the presence of a subterranean hydrocarbon deposit is indicated.

Even though all of curves A shown in FIGS. 1, 2, 3, and 4 generally differ, all are distinctly recognizable as different from the relatively constant distribution shown by curve B of FIG. 1. Thus curves A of FIGS. 1, 2, 3 and 4 all indicate that a hydrocarbon deposit will likely be found under the locations where the samples were taken because a distinct discontinuity occurs in the curve in the vicinity of the maximum depth of surface water penetration. The various shapes of curves A in FIGS. 1, 2, 3 and 4 may be attributable to other competing environmental conditions, such as leaching of magnetic materials from the surface and very near-surface by surface water or the like and because of variations in the constitution and composition of the earth's surface above the level of maximum surface water penetration.

While the method described hereinabove is not represented to be a foolproof method of determining the presence of an underground deposit of hydrocarbon, it serves as a valuable tool, when used in combination with other data, to increase the likelihood of finding an underground deposit of hydrocarbon in an area suspected of containing same.

As noted above, the method of prospecting described entails taking test samples of the earth at various levels in the crust surface subject to oxidation by surface-originated conditions. Thus such test holes may be very quickly and easily made without suffering the expense of a test hole to the suspected depth of the deposit. Obviously, data reliability increases with frequency of sampling. In most cases, samples taken at about ten foot intervals are sufficient to produce reliable information. In some near-surface regions, the geologic composition may vary radically with depth. Thus more frequent sampling may be required. In most cases, sampling as infrequently as thirty foot intervals is probably the outer extreme of frequency acceptable. Sampling at about ten to twenty foot intervals is ordinarily preferred.

The method of the invention may also serve as a valuable tool in determining the approximate horizontal boundaries of a known reservoir. For example, magnetic susceptibility tests may be made on earth samples taken at various depths in a known producing borehole or multiple producing boreholes in the same field to generate a magnetic susceptibility distribution curve characteristic of that particular field. Since the near-surface conditions overlying any one field do not vary dramatically through the horizontal boundaries of the field, multiple test holes can be drilled at various lateral distances in all directions from a producing well and samples taken therefrom. By using the method of the invention, the horizontal boundaries of the field can be determined by comparing the magnetic susceptibility versus depth curves of the various test holes with a general curve generated from data taken from the producing wells.

It would be expected that reducing hydrocarbons migrating from a subterranean deposit will generally migrate and diffuse toward the surface without substantial lateral expansion. Thus the geographic boundaries of the deposit can be readily determined at the surface without driling deep test holes at various lateral distances from the producing holes. Obviously, this technique may eliminate much of the expense incurred in the traditional hit-or-miss technique of drilling such test holes to the known producing depth.

It should be noted that knowledge of the actual chemical compositions of the diagenetic magnetic materials is not necessary to practice the invention as described above since only the relative magnetic intensity distribution is determined. Likewise, the exact depth of surface water penetration need not be precisely determined. Since the invention relies on determination of relative concentrations of diagenetic magnetic materials and natural geologic concentrations of magnetic materials, it is only necessary to determine that an anomaly exists in the concentration of magnetic materials in the vicinity of the maximum depth at which ferrous compounds can be oxidized by surface-controlled conditions. Since the major source of oxygen enrichment of the earth's crust is by penetration of oxygen-rich surface water, the maximum depth of surface water penetration is a convenient reference level. Even though this level may not be well-defined, it can generally be estimated with sufficient detail by reference to the magnetic data since below this level variations in concentration of magnetic material is primarily related to geologic formation.

As noted above, the invention is based on determination of relative concentrations of diagenetic magnetic materials containing iron which have been reduced by hydrocarbons diffusing through the strata. It has been determined that in on-shore locations the magnetic material found in the near-surface directly over known hydrocarbon deposits is principally maghemite ($\gamma Fe_2O_3$). Therefore, chemical or physical analysis of the samples upon which the magnetic susceptibility tests are made to determine the actual chemical constitution of the magnetic material may be used to even further indicate the likelihood of a subterranean petroliferous deposit. Further still, since the chemical composition and physical structure of the product ultimately formed by the reduction and oxidation processes is known, magnetic susceptibility data need not be taken. Instead, the relative concentration of maghemite may be determined by any available means.

As indicated above, the principles of the invention may be applied to off-shore locations as well as on-shore locations. Even where the earth's surface is covered with a body of water, the upward migration of hydrocarbon gas from the subterranean deposit reduces iron in the geologically formed strata thereover, thus producing ferromagnetic iron. However, the ferromagnetic material is converted primarily to ferrous sulfides such as greigite ($Fe_3S_4$) by bacterial activity on water-borne sulfates, ferrous materials and hydrocarbons. Thus, while the general principles are the same whether the invention is used in connection with on-shore or off-shore exploration, the chemical compositions of the diagenetically created magnetic materials may differ.

As described hereinabove, where the earth's surface is not submerged under a body of water, oxidation of near-surface materials to form maghemite is primarily the result of surface water penetration. However, in off-shore locations, the actual earth's surface is submerged under a body of water and the near-surface is in a somewhat oxygen-starved condition. However, organic decomposition still occurs by anoxic processes, particularly bacterial sulfate reduction. Thus, where geologic iron has been reduced by upward migration of hydrocarbons, the ferrous materials are converted to pyrite and/or greigite by reaction with by-products (such as $H_2S$) of the sulfate reduction process. Therefore, the ferrous materials are not oxidized by surface water (as in on-shore locations), but are converted to magnetic sulfides, primarily greigite.

From the foregoing it will be apparent that the methods of the invention provide highly utilitarian and reasonably inexpensive methods of prospecting for subterranean hydrocarbon deposits in areas suspected of containing them. While the invention has been described with particular reference to the depth of maximum penetration of atmospheric oxygen contained in surface water (for on-shore locations), it should be realized that this level is taken as a convenient measure of the depth to which ferrous iron may be oxidized by one-shore surface-related conditions.

In off-shore locations, the maximum depth reference point for which surface-related conditions can be expected to affect the concentration of greigite is the depth to which sufficient surface oxygen can penetrate to support the biological activity necessary to convert water-borne sulfates and geologic iron to greigite. Since this occurs beneath a body of water, the penetration depth may be much less than the penetration depth of surface water observed in on-shore locations. Accordingly, the sampling frequency with depth should ordinarily be more rapid in off-shore locations. In the preferred method of practicing the invention in off-shore situations, earth samples should be taken at approximately ten to twenty centimeter intervals.

It will be readily recognized that conditions at or very near the earth's surface may produce anomalous results because of natural or unnatural surface conditions. For example, relatively recently-occurring surface changes such as could result from agricultural or industrial activities in the vicinity may have disturbed the naturally-occurring variations in relative concentrations of magnetic materials. Furthermore, it should be noted that the concentrations of magnetic materials in the earth's crust normally vary widely from geographic location to geographic location. Thus relative concentration distribution curves of magnetic materials near the surface may vary widely from location to location but will assume relatively similar characteristics within a geographic location suspected of containing a hydrocarbon deposit. Accordingly, while the invention has been described with particular reference to specific embodiments thereof, the forms of the invention shown and described in detail are to be taken as preferred embodiments of same. Various changes and modifications may be restored to without departing from the spirit and scope of the invention as defined by the appended claims.

What is claimed is:

1. The method of prospecting for conditions indicative of subterranean deposits of hydrocarbon comprising the steps of:
    (a) determining the approximate maximum depth of diagenetically-formed magnetic materials in a substantially vertical column of earth;
    (b) taking earth samples from said substantially vertical column of earth at pre-selected depths from the earth's surface to approximately said maximum depth of diagenetically-formed magnetic materials;
    (c) determining the magnetic susceptibility of said earth samples;
    (d) correlating the magnetic susceptibility data of said samples to form a curve representative of the distribution of magnetic susceptibility as a function of depth;
    (e) comparing the magnetic susceptibility distribution curve to the approximate maximum depth of diagenetically-formed magnetic materials; and
    (f) determining if a discontinuity occurs in the magnetic susceptibility distribution curve above the depth representative of the approximate maximum depth of diagenetically-formed magnetic materials in said vertical column of earth.

2. The method set forth in claim 1 wherein said earth samples are taken at progressively deeper known depths from the earth's surface to a depth approximating the maximum depth of diagenetically-formed magnetic materials.

3. The method set forth in claim 1 wherein said earth samples are taken at progressively deeper known depths from the earth's surface to a known depth exceeding the maximum depth of diagenetically-formed magnetic materials.

4. The method set forth in claim 1 wherein said earth samples are taken until a distinct discontinuity in the distribution curve of magnetic susceptibility as a function of depth occurs.

5. The method set forth in claim 1 wherein said earth samples are taken at intervals of approximately ten to approximately twenty feet.

6. The method of estimating the general surface boundary outline of a known subterranean deposit of hydrocarbons comprising the steps of:
    (a) taking earth samples at various known depths from the earth's surface in at least one borehole extending from the earth's surface to said subterranean deposit;
    (b) measuring the magnetic susceptibility of said earth samples;
    (c) correlating the magnetic susceptibilty data of said earth samples to form a curve representative of the distribution of magnetic susceptibility as a function of depth for said borehole;
    (d) determining the approximate maximum depth of diagenetically-formed magnetic materials in the vicinity of said borehole;
    (e) taking earth samples at various known depths between the earth's surface and the approximate maximum depth of diagenetically-formed magnetic materials in a plurality of substantially vertical columns of earth laterally displaced from said borehole;
    (f) measuring the magnetic suseptibility of said earth samples;

(g) correlating the magnetic susceptibility data of the samples from each of said substantially vertical columns to form a curve representative of magnetic susceptibility as a function of depth for each of said plurality of substantially vertical columns; and (h) comparing the curves of magnetic susceptibility as a function of depth for each of said plurality of substantially vertical columns to the curve of magnetic susceptibility as a function of depth for said borehole.

7. The method set forth in claim 6 wherein the maximum depth from which the samples are taken in said plurality of substantially vertical columns is less than the maximum depth of surface water penetration.

8. The method set forth in claim 6 wherein the maximum depth from which the samples are taken in said plurality of substantially vertical columns is greater than the maximum depth of surface water penetration.

9. The method set forth in claim 6 wherein said earth samples are taken at intervals of approximately ten to approximately twenty feet.

10. The method set forth in claim 6 wherein the maximum depth at which earth samples are taken in each of said plurality of vertical columns is the depth at which a distinct decrease in relative concentration of magnetic materials occurs.

11. The method set forth in claim 6 wherein said curve representative of the distribution of magnetic susceptibility as a function of depth for said borehole is produced from data taken at various known depths in a plurality of boreholes extending from the earth's surface to the same subterranean deposit of hydrocarbon.

12. The method of prospecting for conditions indicative of subterranean deposits of hydrocarbon comprising the steps of:

(a) determining the approximate maximum depth at which diagenetic magnetic materials ordinarily exist in a substantially vertical column of earth extending downwardly from the earth's surface in a geographic area in which subterranean deposits of hydrocarbon are suspected to exist;

(b) taking earth samples in said substantially vertical column of earth at pre-selected depths from the earth's surface to a depth greater than the depth at which diagenetic magnetic materials ordinarily exist;

(c) measuring the magnetic susceptibility of said earth samples;

(d) correlating the magnetic susceptibility data of said samples to form a curve representative of the distribution of magnetic susceptibility as a function of depth; and (e) comparing the relative concentration distribution of diagenetic magnetic materials in said column near the earth's surface to the relative concentration distribution of geologic magnetic material at depths greater than the depth at which diagenetic magnetic materials ordinarily exist to determine if a significant discontinuity in the relative concentration of magnetic materials exists at approximately the maximum depth at which diagenetic magnetic materials ordinarily exist.

13. The method of prospecting for conditions indicative of subterranean deposits of hydrocarbon comprising the steps of:

(a) taking earth samples in a substantially vertical column of earth at pre-selected depths from the earth's surface;

(b) determining the concentration of maghemite in said earth samples;

(c) determining the approximate maximum depth of diagenetically-formed magnetic materials in said vertical column;

(d) correlating concentration of maghemite with increasing depth in said column to form a curve representative of the relative concentration of maghemite as a function of depth; and (e) determining if a discontinuity in the distribution curve of maghemite concentration as a function of depth occurs above the approximate maximum depth of diagenetically-formed magnetic materials by comparing the relative concentration distribution of maghemite as a function of depth represented by the portion of said curve above the approximate maximum depth of diagenetically-fromed magnetic materials to the relative concentration distribution of maghemite as a function of depth represented by the portion of said curve below the approximate maximum depth of diagenetically-formed magnetic materials.

14. The method set forth in claim 13 wherein said earth samples are taken at progressively deeper known depths from the earth's surface to a depth approximating the maximum depth of diagenetically-formed magnetic materials.

15. The method set forth in claim 13 wherein said earth samples are taken at progressively deeper known depths from the earth's surface to a known depth exceeding the maximum depth of diagenetically-formed magnetic materials.

16. The method set forth in claim 13 wherein said earth samples are taken until a distinct dicontinuity in the distribution curve of maghemite concentration as a function of depth occurs.

17. The method set forth in claim 13 wherein said earth samples are taken at intervals of approximately ten to approximately twenty feet.

18. The method of estimating the general surface boundary outline of a known subterranean deposit of hydrocarbons comprising the steps of:

(a) taking earth samples at various known depths from the earth's surface in at least one borehole extending from the earth's surface to said subterranean deposit;

(b) measuring the maghemite concentration in said earth samples;

(c) correlating the maghemite concentration of said earth samples to form a curve representative of the relative distribution of maghemite concentration as a function of depth for said borehole;

(d) determining the approximate maximum depth of diagenetically-formed magnetic materials in the vicintity of said borehole;

(e) taking earth samples at various known depths between the earth's surface and the approximate maximum depth of diagenetically-formed materials in a plurality of substantially vertical columns of earth laterally displaced from said borehole;

(f) measuring the maghemite concentration of said earth samples;

(g) correlating the maghemite concentration of the samples from each of said substantially vertical columns to form a curve representative of the relative concentration of maghemite as a function of depth for each of said plurality of substantially vertical columns; and (h) comparing the curves of relative distribution of maghemite concentration as a function of depth for each of said plurality of substantially vertical columns to the curve of relative distribution of maghemite concentration as a function of depth for said borehole.

19. The method set forth in claim 18 wherein the maximum depth from which the samples are taken in said plurality of substantially vertical columns is less than the maximum depth of surface water penetration.

20. The method set forth in claim 18 wherein the maximum depth from which the samples are taken in said plurality of substantially vertical columns is greater than the maximum depth of surface water penetration.

21. The method set forth in claim 18 wherein said earth samples are taken at intervals of approximately ten to approximately twenty feet.

22. The method set forth in claim 18 wherein the maximum depth at which earth samples are taken in each of said plurality of vertical columns is the depth at which a distinct decrease in relative concentration of maghemite occurs.

23. The method set forth in claim 18 wherein said curve representative of the relative distribution of maghemite concentration as a function of depth for said borehole is produced from data taken at various known depths in a plurality of boreholes extending from the earth's surface to the same subterranean deposit of hydrocarbon.

24. The method of prospecting for conditions indicative of subterranean deposits of hydrocarbon comprising the steps of:

(a) determining the approximate maximum depth at which diagenetic magnetic materials ordinarily exist in a substantially vertical column of earth;

(b) taking earth samples in said substantially vertical column of earth at pre-selected depths from the earth's surface to a depth greater than the depth at which diagenetic magnetic materials ordinarily exist;

(c) measuring the maghemite concentration of said earth samples;

(d) correlating maghemite concentration of said samples to form a curve representative of the relative maghemite concentration as a function of depth; and (e) comparing the relative concentration distribution of maghemite in said column near the earth's surface to the relative concentration of maghemite at depths greater than the depth at which diagenetic magnetic materials ordinarily exist to determine if a significant discontinuity in the relative concentration of maghemite occurs near the approximate maximum depth of which diagenetic magnetic materials ordinarily exist in said column of earth.

25. The method of prospecting for conditions indicative of subterranean deposits of hydrocarbon where the earth's surface is covered with a body of water comprising the steps of:

(a) taking earth samples in a substantially vertical column of earth at pre-selected depths from the earth's surface;

(b) determining the greigite concentration in said earth samples;

(c) determining the approximate maximum depth of diagenetically-formed magnetic materials in said vertical column;

(d) correlating greigite concentration with increasing depth in said column to form a curve representative of the relative concentration of greigite as a function of depth; and (e) determining if a discontinuity in the distribution curve of greigite concentration as a function of depth occurs above the approximate maximum depth of diagenetically-formed magnetic materials by comparing the relative concentration distribution of greigite as a function of depth represented by the portion of said curve above the approximate maximum depth of diagenetically-formed magnetic materials to the relative concentration distribution of greigite as a function of depth represented by the portion of said curve below the approximate maximum depth of diagenetically formed magnetic materials.

26. The method set forth in claim 25 wherein said earth samples are taken at progressively deeper known depths from the earth's surface to a depth approximating the maximum depth of diagenetically-formed magnetic materials.

27. The method set forth in claim 25 wherein said earth samples are taken at progressively deeper known depths from the earth's surface to a known depth exceeding the maximum depth of diagenetically-formed magnetic materials.

28. The method set forth in claim 25 wherein said earth samples are taken until a distinct discontinuity in the distribution curve of greigite conentration as a function of depth occurs.

29. The method set forth in claim 25 wherein said earth samples are taken at intervals of approximately ten to approximately twenty centimeters.

30. The method of estimating the general surface boundary outline of a known subterranean deposit of hydrocarbons where the earth's surface is covered with a body of water comprising the steps of:

(a) taking earth samples at various known depths from the earth's surface in at least one borehole extending from the earth's surface to said subterranean deposit;

(b) measuring the greigite concentration in said earth samples;

(c) correlating the greigite concentration data of said earth samples to form a curve representative of relative greigite concentration as a function of depth for said borehole;

(d) determining the approximate maximum depth of diagenetically-formed magnetic materials in the vicinity of said borehole;

(e) taking earth samples at various known depths between the earth's surface and the approximate maximum depth of diagenetically-formed magnetic materials in a plurality of substantially vertical columns of earth laterally displaced from said borehole;

(f) measuring the greigite concentration in said earth samples;

(g) correlating the greigite concentration data of the samples from each of said substantially vertical columns to form a curve representative of relative greigite concentration as a function of depth for each of said plurality of substantially vertical columns; and (h) comparing the curves of relative greigite concentration as a function of depth for each of said plurality of substantially vertical columns to the curve of relative greigite concentration as a function of depth for said borehole.

31. The method as set forth in claim 30 wherein the maximum depth from which the samples are taken in said plurality of substantially vertical columns is less than the maximum depth of ocean water penetration.

32. The method set forth in claim 30 wherein the maximum depth from which the samples are taken in said plurality of substantially vertical columns is greater than the maximum depth of ocean water penetration.

33. The method set forth in claim 30 wherein said earth samples are taken at intervals of approximately ten to approximately twenty centimeters.

34. The method set forth in claim 30 wherein the maximum depth at which earth samples are taken in each of said plurality of vertical columns is the depth at which a distinct decrease in relative greigite concentration occurs.

35. The method set forth in claim 30 wherein said curve representative of relative greigite concentration as a function of depth for said borehole is produced from the data taken at various known depths in a plurality of boreholes extending from the earth's surface to the same subterranean deposit of hydrocarbon.

36. The method of prospecting for conditions indicative of subterranean deposits of hydrocarbon where the earth's surface is covered with a body of water comprising the steps of:
    (a) determining the approximate maximum depth at which diagenetic magnetic materials ordinarily exist in a substantially vertical column of earth;
    (b) taking in earth samples in said substantially vertical column of earth at pre-selected depths from the earth's surface to a depth greater than the depth at which diagenetic magnetic materials ordinarily exist;
    (c) measuring the greigite concentration in said earth samples;
    (d) correlating greigite concentration of said samples to form a curve representative of the relative greigite concentration as a function of depth; and
    (e) comparing the relative concentration distribution of greigite in said column near the earth's surface with respect to the relative concentration of greigite distribution at depths greater than the depth at which diagenetic magnetic materials ordinarily exist to determine if a significant discontinuity in the relative concentration of greigite occurs near the approximate maximum depth at which diagenetic magnetic materials ordinarily exist.

37. The method set forth in claim 1 wherein said earth samples are taken at intervals of approximately ten to approximately twenty centimeters.

* * * * *

UNITED STATES PATENT AND TRADEMARK OFFICE
CERTIFICATE OF CORRECTION

PATENT NO. : 4,729,960

DATED : March 8, 1988

INVENTOR(S) : Robert S. Foote

It is certified that error appears in the above-identified patent and that said Letters Patent is hereby corrected as shown below:

```
Column 1, line 25   change "(Fee+++)" to ---(Fe+++)---
Column 3, line 9    change "everincreasing" to ---ever-increasing---
Column 3, line 13   delete "of"
Column 3, line 33   delete "of" (second occurrence)
Column 4, line 37   after "data" insert ---for---
Column 7, line 26   change "them." to ---same.---
Column 7, line 31   change "one-shore" to ---on-shore---
Column 7, line 67   change "restored" to ---resorted---
Column 13, line 6   delete "as"
Column 14, line 6   delete "in" (first occurrence)
```

Signed and Sealed this

Thirteenth Day of September, 1988

Attest:

DONALD J. QUIGG

*Attesting Officer*    *Commissioner of Patents and Trademarks*